(12) United States Patent
Sauerland

(10) Patent No.: US 6,810,742 B2
(45) Date of Patent: Nov. 2, 2004

(54) METHOD OF AND AN APPARATUS FOR DETERMINING THE SPEED OF SOUND IN A MATERIAL

(75) Inventor: Martin Sauerland, Mönchengladbach (DE)

(73) Assignee: SMS Meer GmbH, Moncnengladbach (DE)

( * ) Notice: Subject to any disclaimer, the term of this patent is extended or adjusted under 35 U.S.C. 154(b) by 0 days.

(21) Appl. No.: 10/446,503

(22) Filed: May 28, 2003

(65) Prior Publication Data

US 2003/0221490 A1 Dec. 4, 2003

(30) Foreign Application Priority Data

May 29, 2002 (DE) .......................................... 102 23 786

(51) Int. Cl.[7] .............................................. G01N 29/04
(52) U.S. Cl. ............................. 73/597; 73/598; 73/602; 73/655; 356/502
(58) Field of Search .......................... 73/597, 598, 600, 73/602, 596, 643, 644, 655; 356/502, 432

(56) References Cited

U.S. PATENT DOCUMENTS

| | | | | |
|---|---|---|---|---|
| 3,943,755 A | * | 3/1976 | Arii et al. ..................... | 73/597 |
| 4,246,793 A | * | 1/1981 | Fairand et al. ................. | 73/628 |
| 4,567,770 A | * | 2/1986 | Rumbold et al. ............. | 73/644 |
| 5,379,270 A | * | 1/1995 | Connolly ..................... | 367/128 |
| 5,648,611 A | * | 7/1997 | Singh et al. .................. | 73/598 |
| 5,684,252 A | * | 11/1997 | Kessler et al. ................ | 73/618 |
| 6,069,703 A | * | 5/2000 | Banet et al. ................. | 356/432 |
| 6,175,416 B1 | * | 1/2001 | Maris et al. ................. | 356/630 |
| 6,400,449 B2 | * | 6/2002 | Maris et al. .................. | 356/72 |
| 6,628,404 B1 | * | 9/2003 | Kelley et al. ............... | 356/502 |

FOREIGN PATENT DOCUMENTS

| | | |
|---|---|---|
| CA | 2 187 957 | 6/2003 |
| DE | 1 248 347 | 2/1963 |
| EP | 0 940 193 | 9/1999 |
| GB | 2 114 297 | 9/1971 |

* cited by examiner

Primary Examiner—Hezron Williams
Assistant Examiner—Jacques M. Saint-Surin
(74) Attorney, Agent, or Firm—Herbert Dubno

(57) ABSTRACT

The speed of sound c is determined in a material as a function of the temperature T by heating an end of an elongated sample body of the material of the temperature and determining the time difference for the receipt of echoes from two reflective zones at the heated end. The opposite end of the body is cooled in a water bath which can couple an ultrasonic test head to the body.

18 Claims, 3 Drawing Sheets

US 6,810,742 B2

METHOD OF AND AN APPARATUS FOR DETERMINING THE SPEED OF SOUND IN A MATERIAL

FIELD OF THE INVENTION

My present invention relates to a method of and an apparatus for determining the speed of sound in a material as a function of its temperature.

BACKGROUND OF THE INVENTION

For many applications a steel pipe or tubing is required which is seamless and is fabricated by passing a cylindrical solid workpiece of steel between a pair of mutually inclined rolls which cooperate with a fixed mandrel to form a passage in the workpiece. The production of seamless tubing by rolling the material over a mandrel is described, for example, in EP 0 940 193 A2. This method is known variously as the piercing process and the roll-forging process. In a stretch-reducing rolling and through the use of reducing rolling and dimensional rolling, a seamless steel pipe or tubing can be fed through a multiplicity of roll stands and the desired dimensions can be imparted to the workpiece so that a particular cross section is obtained. In each roll frame there may be three rolls which enable the pipe or tubing to be engaged on all sides. The rolling will generally reduce the diameter and impart a precise shape to the product.

The pipe or tubing after rolling should have an ideal shape in that the cylindrical contours of the inner and outer peripheries should correspond to two precisely concentric circles. In practice, however, there are always fabrication tolerances so that there is always some eccentricity of the circular contour of the interior of the workpiece relative to the circular contour of the exterior thereof.

This effect can be measured by detecting the wall thickness of the tubing and the process can be controlled in response to monitoring the wall thickness.

To detect the wall thickness and derive therefrom signals which can be used to control the process or to signal the wall thickness and thus the ability of the workpiece to meet tolerance requirements, especially for the hot workpieces, earlier methods have utilized laser and ultrasonic measurement techniques. Ultrasonic thickness measurements utilize a pulse echo method which, from a transit time of an ultrasonic pulse, can calculate the wall thickness. For this, however, it is necessary to know the speed of sound in the material of the workpiece at the temperature of the workpiece at which the measurement is to be made. The speed of sound in the material is thus dependent both upon workpiece composition and on the temperature.

From Canadian patent 2 187 957 A1, it is known to use ultrasonic pulses and monitoring for controlling process conditions in liquid metals. The principle involved is also a pulse echo method which evaluates the reflected ultrasound pulses.

For determining the speed of sound in materials at predetermined temperatures, a variety of methods have been proposed.

The speed of sound, for example, at a certain temperature can be obtained by interpolation of values obtained from tables. The disadvantage of this approach is that often the values obtained are not sufficiently precise to enable a highly precise determination of a wall thickness as may ultimately be required.

Another method of determining the speed of sound at a certain temperature is to heat a tubular sample with a known wall thickness to the desired temperature and using a wall thickness measuring device which operates based upon the laser-ultrasound high wall thickness measuring technique, namely a pulse-echo method, measuring the wall thickness. From the known wall thickness the speed of sound in the material can be determined by detecting the time interval between the applied signal and the echo and calculate it back based upon the temperature.

A disadvantage of this technique, however, is that at high temperatures tubular samples which are used rapidly tend to scale and develop oxide films or coatings or falsify the measurement results. Furthermore, at the measuring points material must be removed because of the scaling to allow the laser-ultrasound hot wall thickness measurement technique to be employed so that the sample must be removed between two measurements.

OBJECTS OF THE INVENTION

It is, therefore, the principal object of the present invention to provide an improved method and apparatus with which these drawbacks can be obviated, namely, a method of and an apparatus which will allow the speed of sound in a material to be obtained without concern for scaling and in a highly precise and reproducible manner which especially enables thickness measurements to be calculated by the pulse-echo technique.

Another object of this invention is to provide a method of measuring the speed of sound in a workpiece which is simple and effective, does not require significant movement of the material in which the measurement is to be made, and can provide results of such precision that wall and other calculations can be made with high precision.

SUMMARY OF THE INVENTION

These objects are achieved, in accordance with the invention in a method of determining the speed of sound in a material as a function of the temperature by:

a) Initially preparing a sample body which is elongated, composed of the material in which the speed of sound is to be measured and which is formed preferably at one of its end regions with two reflection zones at a predetermined distance or spacing form one another.

b) Then at least the end region of the sample body provided with those reflection zones is heated to a temperature at which the speed of sound is to be determined.

c) An ultrasonic signal is then applied to the sample body.

d) The time interval is then measured between two ultrasonic echo signals emitted by the sample body and resulting from reflections of the ultrasonic signal applied to the sample body at the two reflection zones.

e) Finally the speed of sound is calculated as a quotient of the spacing between the reflection zones and the measured time interval.

More specifically the method of determining the speed of sound (c) in a material as a function of the temperature (T) can comprise the steps of:

(a) providing a sample body of the material at an end segment with two sound-reflection zones at a predetermined distance apart (a) in a longitudinal direction in the sample body;

(b) heating at least the end segment of the sample body to a temperature (T) at which a speed of sound (c) is to be determined;

(c) launching an ultrasonic signal into the sample body;

(d) measuring a time interval (Δt) between respective ultrasonic echo signals generated at the sound-reflection zones; and (e) calculating the speed of sound (c) as the quotient of the distance (a) and the time interval (Δt) (c=a/Δt) for the temperature (T) to which the end segment is heated.

To determine the functional relationship between the speed of sound and the temperature, the steps (b) to (e) are repeated at different temperatures (T). When the sample is composed of metal, especially steel, the measurement of the speed of sound is preferably carried out at temperatures between room temperature and 1200° C. in steps of 50 K. The measurement of the speed of sound at temperatures between room temperatures and 600° C. can be made in steps of 100 K.

Advantageously, the two reflection zones are provided in an end region of the sample body which is uniformly heated and indeed thus can be the only part of the body which is uniformly heated. The opposite end, i.e. the end opposite the end which is heated, can be cooled and cooling can be provided for all of the nonheated parts of the sample body.

The ultrasonic signal which is launched into a sample body can be applied thereto at the end opposite the heated end and preferably from a piezoultrasonic element which can be coupled to the sample body by water coupling.

The apparatus for determining the speed of sound can comprise:

a heater for heating an end segment of an elongated sample body of the material provided with two sound-reflection zones at a predetermined distance apart (a) in a longitudinal direction in the sample body to a temperature (T) at which a speed of sound (c) is to be determined;

means for launching an ultrasonic signal into the sample body;

means for measuring a time interval (Δt) between respective ultrasonic echo signals generated at the sound-reflection zones; and means for calculating the speed of sound (c) as the quotient of the distance (a) and the time interval (Δt) (c=a/Δt) for the temperature (T) to which the end segment is heated.

The sample body is preferably a round rod or a flat bar composed of the material in which the speed of sound is to be determined. The reflection zones can be formed as notches matched in the sample body. Alternatively, they can be formed by providing a step in the sample body. In the latter case the sample body can simply have a cross section reduction which is of a special shape.

The heating means of the end provided with the reflection zones can be a furnace in which the end of the sample body is received or which surrounds this end. The apparatus can also include means for cooling at least the end of the sample body opposite the heated end.

The means for launching the ultrasonic signal into the sample body can be any commercially available piezo test head as may be used for ultrasonic applications although other techniques for generating the ultrasonic signals may be used as well. For example, the transducer for producing the ultrasound may be an EMUS (electromagnetic ultrasound) generator.

It has been found to be advantageous to produce a sample body of a length of 750 to 1250 mm and the two reflection zones in the form of notches in one end of the sample body at a spacing of 50 to 200 mm from one another, preferably at a distance of 100 mm. The sample body can be a round rod whose diameter is between 15 mm and 50 mm and is preferably 30 mm.

With the system of the invention, the formation of scaling on the sample body does not have any effect so that a precise measurement of the sound speed can be obtained. Furthermore, material removal from the sample body by laser light plays no role in determining the sound speed.

The apparatus used can be very simple so that the variation in the sound speed with temperature can be obtained with precision and in spite of the low cost of the apparatus.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
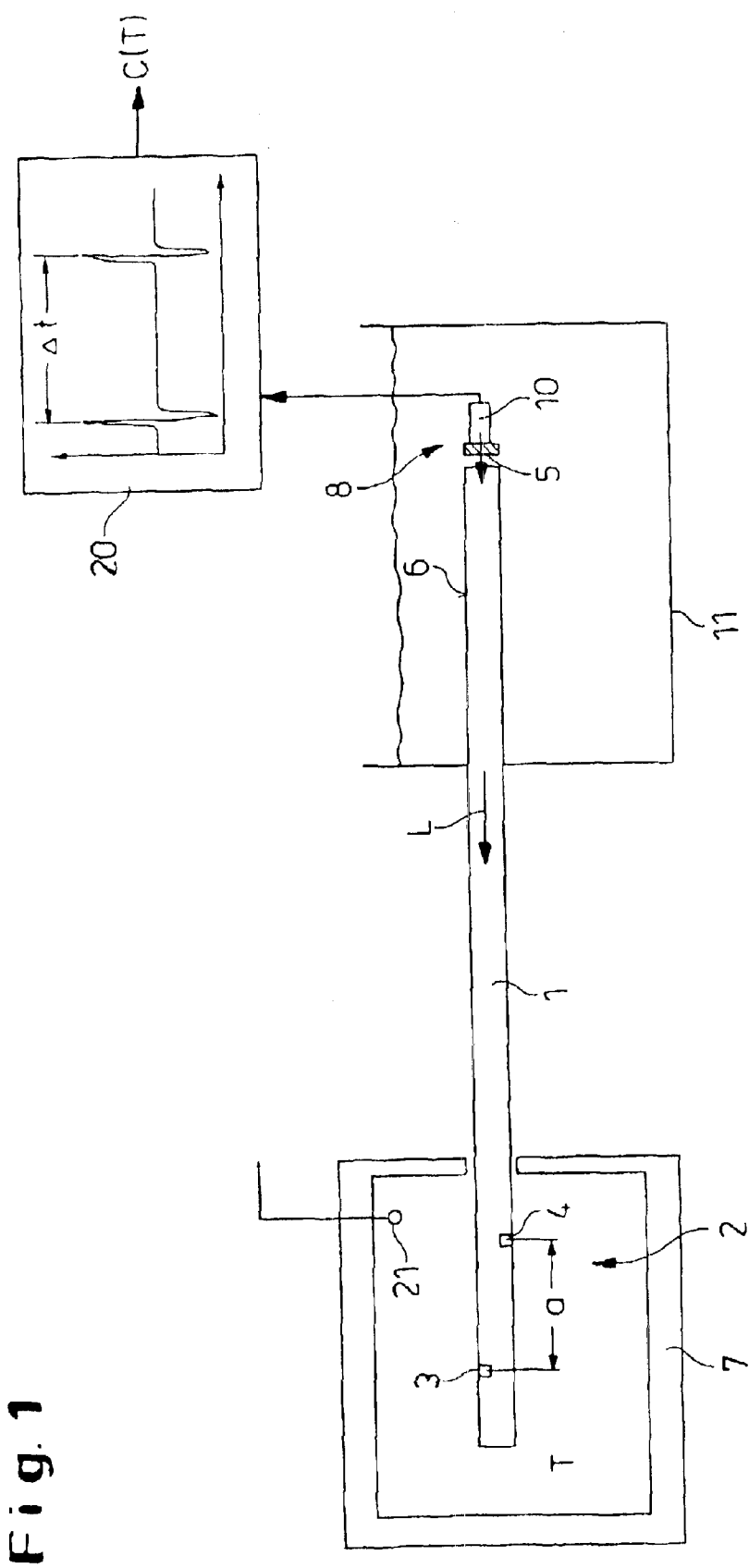
FIG. 1 is a diagrammatic side elevation illustrating the invention.
Figure 3:
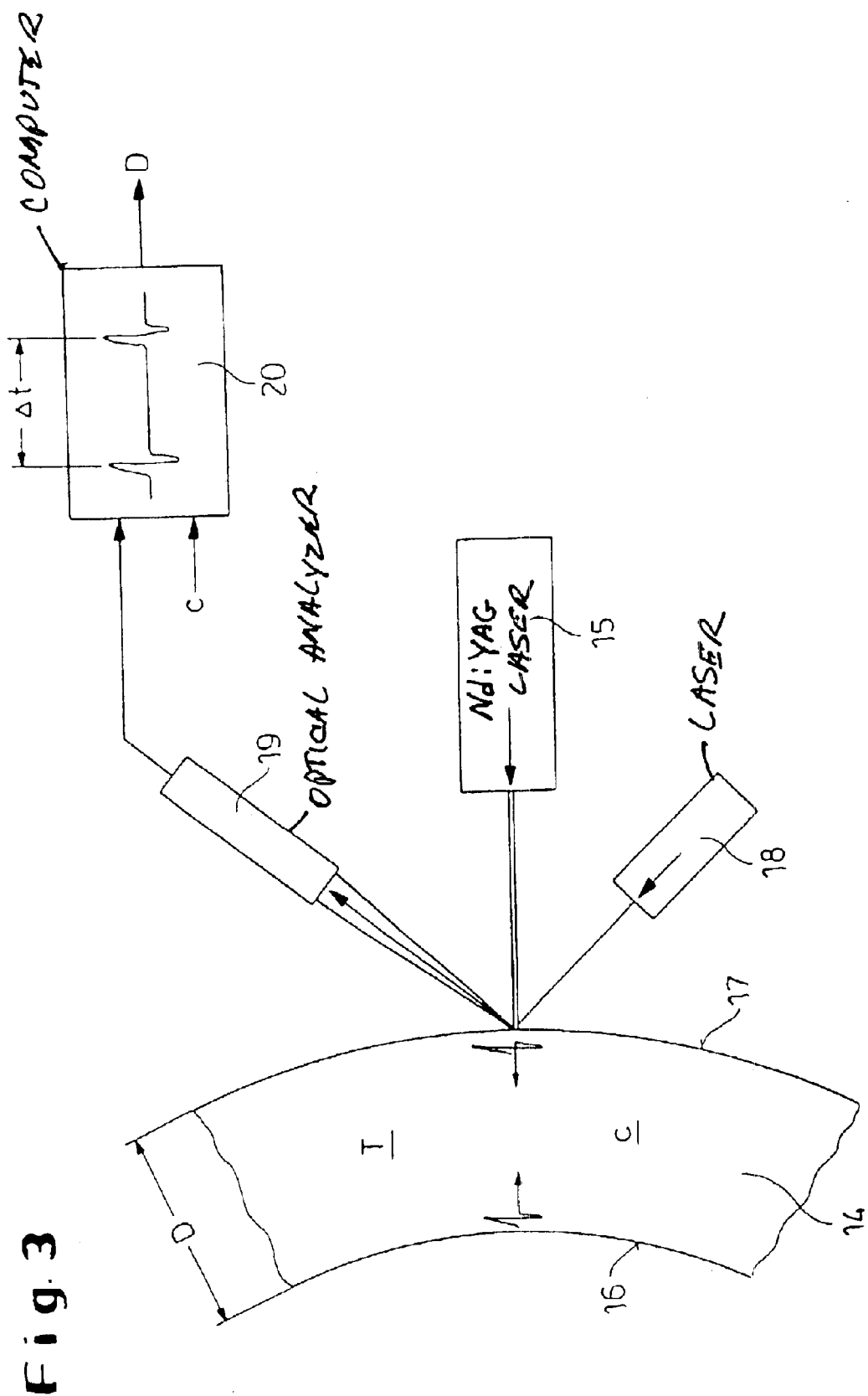
FIG. 3 is a diagram of the determination of the wall thickness of a hot pipe utilizing the laser ultrasound method with the speed of sound information obtained by the system of either FIG. 1 or FIG. 2.

In FIG. 1 I have shown a bar or rod-shaped sample body 1, e.g. of the seam steel as used to make the pipe for tubing of FIG. 3 and which is used to provide a measurement of the speed of sound in that sample body. The speed of sound is represented at c in FIG. 1 and is a function of the temperature T. The sample body 1 is provided with a pair of notches 3 and 4 separated by a spacing a in the longitudinal direction L of the sample body.

The end of the sample body 1 which is provided with the reflection zones formed by the notches 3 and 4 is received in a furnace 7.

The speed of sound c, more particularly at a certain temperature T can be used to precisely measure the wall thickness of a rod seamless tube 14 utilizing the system schematically shown in FIG. 3. This system utilizes the laser-ultrasound hot wall measurement process, in which the transit time for an ultrasound pulse applied to the outer periphery 17 of the tube 14 passes to the inner periphery 16 and is reflected back to the outer periphery. The transit time across twice the thickness D is measured and the product of the speed c and this transmit time is equal to 2D.

The temperature of the rolled tube 14 is represented at T in FIG. 3 and can be about 1000° C., and because of this high temperature, the measurement head is usually spaced from the hot tube and the measurement is carried out in a contactless manner from the exterior.

High energy light pulses in the infrared range are absorbed at the pipe surface 17. They are directed from an Nd:YAG laser 15 which can be pumped y a flash lamp, onto the surface of the seamless tube 14. Alternatively, an ultrasonic signal can be transmitted to the tube with a wavelength 1.064 and a pulse duration of less than 10 ns from an electromagnetic ultrasonic generator (EMUS) or a piezoultrasonic generator.

When a laser 15 is used, the laser energy absorbed by the tube wall is partly converted to the ablation of a very thin layer of the surface of the tube in the nm range which produces an evaporation pulse which corresponds to an ultrasonic pulse and is transmitted through the all of the tube 14 perpendicular to the outer surface. The echo is reflected from the inner surface back toward the outer surface and can be picked up.

The echo may have a reduced amplitude as shown by the wave symbols launched through the thickness of the tube from right to left reduced amplitude signal reflected from left to right.

The reflected ultrasonic pulse produces at the outer surface 17 of the tube oscillations in a subminiature range which modulate a second laser beam trained from the laser 18 onto the surface. This laser beam can be referred to as a detection laser beam. The modulation utilizes the Doppler effect and is detected by a photo tube or optical analyzer 19.

More particularly, the laser 18 can be a continuous wave laser with a diode pump Nd:YAG laser of the frequency doubling type with a wavelength of 532 nm. The continuous wave laser 18 is trained upon the point at which the laser beam from the laser 15 impinges upon the surface 17.

The frequency modulated light cone which is the carrier of the ultrasonic signal can be picked up by the collecting lens and an optical waveguide of the analyzer 19 and supplied to a demodulator which can be a confocal Fabry-Perot interferometer, whose output at the computer 20 provides directly the thickness D. The ultrasonic signal evaluator 20 which has been indicated to be a computer, can, of course, also provide for further amplification, filtering and signal evaluation for the echo pulse sequence as represented in the block 20. An input at c can be provided for the velocity of the sound in the material. Specifically the computer calculates the product $c\Delta t$ and divides that product by 2 in calculating the thickness D.

Thus it is apparent that the magnitude c is essential for an accurate determination of the wall thickness of the produced seamless tubing.

Returning to FIG. 1, it can be seen that the sample body 1, preferably a round rod of a length of say 1000 mm and a diameter of 30 mm, can have the two refraction zones, 3, 4 milled into it at a precisely determined distance of say a=100 mm. The distance a between the notches 3, 4 forms the measurement stretch. They can be provided along the first 200 mm of the sample body 1.

This region of the sample body is received in the furnace 7 which can be thermostated to the precise temperature T at which the measurement is to be taken. The remainder of the sample body 1 and at least the opposite end thereof can be cooled. For example, at least this end of the body 1 can extend into a water bath 11. The water of this bath serves simultaneously as an acoustic coupler.

An ultrasonic source 8 is juxtaposed with the unheated end 6 of the sample body 1 and can be part of a conventional ultrasonic test head 10 useful in piezoelectric testing of articles. The compression/rarefaction longitudinal waves represented at 5 are transmitted in the longitudinal direction L to the body 1 through the water of the cooling bath 11.

At the notches 3 and 4, sound waves are reflected from left to right in FIG. 1 and hence back toward the end 6. The ultrasonic test head 10 is capable of picking up the notch echoes and is connected to the evaluator unit 20 which converts the echo signals to a measure of the time interval $\Delta t$ between reflected waves and forms the quotient $a/\Delta t$ which, as noted, provides directly the value of the speed of sound at the particular temperature T.

If the temperature T in the furnace is raised at intervals and the measurements repeated, the relationship c=c(T) can be measured. The actual temperature T at each measurement is detected by a sensor 21.

From room temperature to a temperature of 600° C., the measurements are made in steps of 100 K and between 600° C. to 1200° C. the measurements are made in 50 K steps.

Since the measurements of the wall thickness of the pipe are usually taken above 600° C., the temperature range above 600° C. is the most interesting and hence the pattern of measurements in this region is closer. The result is a graph of the speed of sound c as a function of the temperature T which also includes the contribution from the thermal expansion of the material.

Figure 2:
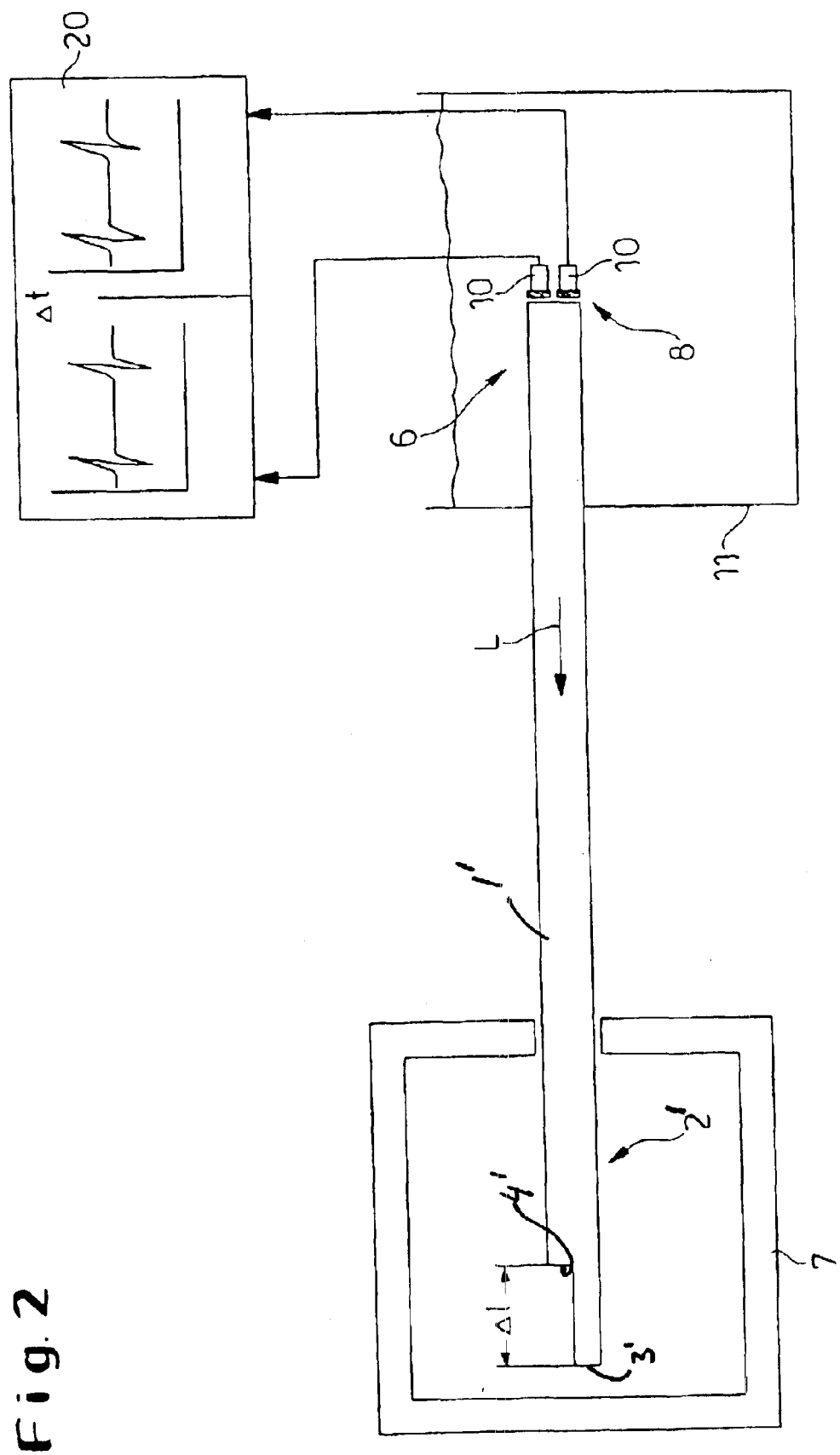
FIG. 2 is a view similar to FIG. 1 of the second apparatus.

FIG. 2 shows an embodiment in which the end region 2' of the sample body 1' is provided with a step $\Delta l$ so that the two reflective regions are the end of the rod 3' and the step 4'. At the opposite end of the body 1' two piezoultrasonic test heads are provided and are connected to the test head electronic circuitry, i.e. the evaluation circuitry 20.

Should the end 2' of the body 1' not be nonuniformly scaled by the heating of the end region, the transit time difference in the reflected wave will provide the requisite information from which the speed of sound c is obtainable in the manner described.

I claim:

1. A method of determining the speed of sound (c) in a material as a function of the temperature (T) of the material, comprising the steps of:
    (a) providing an elongated sample body of said material at an end segment with two sound-reflection zones at a predetermined distance apart (a) in a longitudinal direction in said sample body;
    (b) heating at least said end segment of said sample body to a temperature (T) at which a speed of sound (c) is to be determined;
    (c) launching an ultrasonic signal into said sample body;
    (d) measuring a time interval ($\Delta t$) between respective ultrasonic echo signals generated at said sound-reflection zones;
    (e) calculating the speed of sound (c) as the quotient of the distance (a) and the time interval ($\Delta t$) ($c=a/\Delta t$) for the temperature (T) to which the end segment is heated; and
    (f) cooling at least an end of said sample body opposite said end segment.

2. The method defined in claim 1 wherein steps (b) through (e) are repeated at different temperatures (T).

3. The method defined in claim 2 wherein said material is a metal.

4. The method defined in claim 3 wherein said material is steel and the measurements of the speed of sound (c) are made for temperatures (T) between room temperature and 1,200° C.

5. The method defined in claim 4 wherein said measurements of the speed of sound (c) are made for temperatures (T) between 600° C. and 1,200° C. in steps of 50 K.

6. The method defined in claim 4 wherein the measurement of the speed of sound (c) is made at temperatures between room temperature and 600° C. at temperature steps of 100 K.

7. The method defined in claim 1 wherein all of said body which is not heated in step (b) is cooled.

8. The method defined in claim 1 wherein said ultrasonic signal is launched into said sample body at an end thereof opposite the heated end segment.

9. The method defined in claim 8 wherein said ultrasonic signal is launched into said sample body is coupled to said body from a piezoelectric ultrasonic element with water coupling.

10. An apparatus for determining the speed of sound (c) in a material as a function of the temperature (T) of the material, comprising:
- a heater for heating an end segment of an elongated sample body of said material provided with two sound-reflection zones at a predetermined distance apart (a) in a longitudinal direction in said sample body to a temperature (T) at which a speed of sound (c) is to be determined;
- means for launching an ultrasonic signal into said sample body;
- means for measuring a time interval ($\Delta t$) between respective ultrasonic echo signals generated at said sound-reflection zones; and
- means for calculating the speed of sound (c) as the quotient of the distance (a) and the time interval ($\Delta t$) ($c = a/\Delta t$) for the temperature (T) to which the end segment is heated, said sample body having a length of 750 to 1250 mm and said sound-reflection zones being formed by notches machined in said body at a distance of 50 to 200 mm from one another.

11. The apparatus defined in claim 10 wherein said heater is a furnace.

12. The apparatus defined in claim 11 wherein said sample body is a round or flat bar of said material.

13. The apparatus defined in claim 12 wherein said zones are formed by at least one notch machined in said body.

14. The apparatus defined in claim 12 wherein said zones are formed by at least one cross section reduction formed in said body.

15. The apparatus defined in claim 14 wherein said cross section reduction is in the form of a step.

16. The apparatus defined in claim 10 wherein said distance is about 100 mm.

17. The apparatus a defined in claim 10 wherein said body is a round rod with a diameter of 15 mm to 50 mm.

18. The apparatus defined in claim 17 wherein said diameter is about 30 mm.

\* \* \* \* \*